United States Patent [19]

Edwards

[11] Patent Number: 4,933,502

[45] Date of Patent: Jun. 12, 1990

[54] PROCESS FOR THE PREPARATION OF NONIONIC SURFACTANTS

[75] Inventor: Charles L. Edwards, Houston, Tex.

[73] Assignee: Shell Oil Company, Houston, Tex.

[21] Appl. No.: 201,248

[22] Filed: Jun. 2, 1988

[51] Int. Cl.$^5$ .............................................. C07C 41/03
[52] U.S. Cl. ..................................... 568/618; 568/620
[58] Field of Search ................................ 568/618, 620

[56] References Cited

U.S. PATENT DOCUMENTS 4,721,816  1/1988  Edwards ........................... 568/618

Primary Examiner—Howard T. Mars

[57] ABSTRACT

An improved process for the preparation of narrow-range alkanol alkoylates by the addition reaction of higher alkanols with alkylene oxides, particularly ethylene oxide. U.S. Pat. No. 4,721,816 describes a process in which alkylene oxides are added to alkanols by reaction in the presence of a catalyst prepared by contacting a sulfur-containing acid such as sulfuric acid with one or more aluminum compounds selected from the group consisting of aluminum alcoholates and aluminum phenolates. Under the present invention, that process is improved by carrying out the process in the further presence of water, provided that certain critical restrictions are placed upon the proportions of the water and of the sulfuric acid and aluminum catalyst components. The process improvement of the invention offers substantial improvement in alkoxylation reaction rate and/or selectivity of the reaction to the desired alkanol alkoxylate products, rather than to by-products such as polyalkylene glycols. The narrow-range alkanol alkoxylate products of the process of the invention have utility, for instance, as nonionic surfactant components of detergent formulations.

24 Claims, No Drawings

PROCESS FOR THE PREPARATION OF NONIONIC SURFACTANTS

BACKGROUND OF THE INVENTION

This invention relates to the preparation of nonionic alkanol alkoxylates as the reaction products of alkylene oxides with detergent-range, i.e., $C_8$ to $C_{20}$, alkanols. More particularly, this invention is directed to an improvement in the process for the preparation of such surfactant materials which utilizes an alkoxylation catalyst which combines one or more aluminum compounds with one or more sulfur-containing acids.

Products useful, for instance, as nonionic surfactants, wetting and emulsifying agents, solvents, and chemical intermediates, are prepared by the addition reaction (alkoxylation reaction) of alkylene oxides with detergent-range alkanols. An illustration of the preparation of an alkanol ethoxylate (represented by formula III below) by addition of a number (n) of ethylene oxide molecules (formula II) to a single alkanol molecule (formula I) is presented by the equation

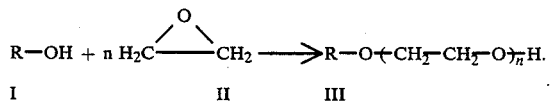

Alkylene oxide addition reactions are known to produce a product mixture of various alkoxylate molecules having different numbers of alkylene oxide adducts (oxyalkylene adducts), e.g., having different values for the adduct number n in formula III above. The adduct number is a factor which in many respects controls the properties of the alkoxylate molecule, and efforts are made to tailor the average adduct number of a product and/or the distribution of adduct numbers within a product to the product's intended service.

In one respect the present invention is a process for the production of an alkanol alkoxylate product having a narrow-range alkylene oxide adduct distribution. Alkoxylate mixtures in which a relatively large proportion of the alkoxylate molecules have a number (n) of alkylene oxide adducts that is within a relatively narrow range of values have been reported as being preferred for use in certain detergent formulations (Great Britain Pat. No. 1,462,134; Derwent Publications Research Disclosure No. 194,010). Narrow-range alkoxylates are also known to be particularly valuable as chemical intermediates in the synthesis of certain carboxyalkylated alkyl polyethers (U.S. Pat. No. 4,098,818) and of certain alkyl ether sulfates (Great Britain Pat. No. 1,553,561).

More particularly, the present invention provides an improvement upon a process described and claimed in the recently issued U.S. Pat. No. 4,721,816, entitled "Preparation of Nonionic Surfactants". That patent discloses that alkanol alkoxylates characterized by a narrow-range alkylene oxide adduct distribution and by a low content of residual alkanol are prepared in a process which comprises contacting and reacting an alkylene oxide reactant comprising one or more $C_2$ to $C_4$ vicinal alkylene oxides with an alkanol reactant comprising one or more $C_6$ to $C_{30}$ alkanols in the presence of a catalytically effective amount of a catalyst prepared by contacting (i) sulfuric acid and (ii) one or more aluminum compounds selected from the group consisting of aluminum alcoholates and aluminum phenolates, the molar ratio of (i) to (ii) being in the range from about 0.1:1 to 2:1.

SUMMARY OF THE INVENTION

In brief summary, the present invention can be described as an improved process for the preparation of narrow-range alkanol alkoxylates by contacting and reacting an alkylene oxide reactant comprising one or more $C_2$ to $C_4$ vicinal alkylene oxides with an alkanol reactant comprising one or more $C_6$ to $C_{30}$ alkanols, in the presence of a catalytically effective amount of a catalyst prepared by contacting (i) sulfuric acid and (ii) one or more aluminum compounds selected from the group consisting of aluminum alcoholates and aluminum phenolates. The improvement particularly comprises carrying out the said contact and reaction in the presence of the combination of the sulfuric acid with the one or more aluminum compounds in specified critical proportions, and further in the presence of a critical quantity of water. More particularly, the invention requires that the molar ratio of the sulfuric acid to the aluminum alcoholates and phenolates be in the range from about 0.2:1 to about 0.7:1 and that the molar ratio of the water to the aluminum alcoholates and phenolates be in the range from about 0.1:1 to about 1.5:1.

The presence of water in the alkoxylation process mixture, in the quantity indicated, substantially improves the performance of the process both from the standpoint of increasing the rate of the alkoxylation reaction and also from the standpoint of enhancing the selectivity of the reaction to the preparation of alkanol alkoxylates.

With respect to process selectivity, the presence of water according to the invention decreases the formation of polyalkylene glycols. Polyalkylene glycols are the principal by-products of the typical alkanol alkyoxylation process, resulting from oligomerization and polymerization of the alkylene oxide reactant. It is considered particularly surprising that the presence of water is responsible for this improvement. In conventional practice, the presence water in alkoxylation processes has been thought to promote, rather than decrease, polyalkylene glycol formation. There are numerous teachings in the art advising that care be taken to remove all water from alkoxylation reaction systems.

DESCRIPTION OF THE PREFERRED EMBODIMENTS

The present invention centers upon discoveries associated with the desirable influence of certain critical quantities of water upon the performance of the alkoxylation process described in U.S. Pat. No. 4,721,816. The invention more particularly centers both upon the presence of water in the reaction system and upon certain critical proportions for water and the two catalyst components. In other respects, the process of the invention is, as a general rule, suitably conducted under the process procedures and conditions described in U.S. Pat. No. 4,721,816. The disclosures of U.S. Pat. No. 4,721,816 are incorporated herein for their teachings of suitable and preferred process procedures and conditions.

In summary, the process of U.S. Pat. No. 4,721,816 (and of this invention) is practiced by contacting the alkylene oxide reactant and the active hydrogen reactant in the presence of the catalyst system comprising the sulfur-containing acid (in the case of the invention, sulfuric acid) and the one or more aluminum alcoholates and phenolates. The alkylene oxide reactant comprises one or more $C_2$ to $C_4$ vicinal alkylene oxides. Reactants which comprise ethylene oxide, propylene oxide or mixtures of ethylene oxide and propylene oxide are preferred, while reactants wherein the alkylene oxide content consists essentially of ethylene oxide are considered particularly preferred. The alkanol reactant suitably comprises one or more alkanols having carbon numbers in the range from about 6 to 30. An alkanol reactant consisting essentially of primary, mono-hydric alkanols is considered most preferred, although secondary and tertiary alkanols, as well as poly-hydric alkanols, are also very suitably utilized in the process either alone or in mixtures with the primary mono-hydric alkanols. Most preferably, the alkanol reactant consists essentially of one or more $C_6$ to $C_{30}$ primary mono-hydric alkanols. Further preference can be expressed for alkanols having from 8 to 20 carbon atoms, with $C_{11}$ to $C_{16}$ alkanols considered more preferred. As a general rule, the carbon chains of the alkanols may be of either branched or linear (straight chain) structure, although preference exists for predominantly linear alkanols in which greater than about 50 percent, more preferably greater than about 70 percent and most preferably greater than about 90 percent, of the molecules are of linear carbon structure. The two reactants are utilized in quantities which are predetermined to yield an alkoxylate product of the desired mean or average adduct number. The invention is most effective for the preparation of adducts characterized by an average of up to about 4 mols of alkylene oxide per mol of alkanol, particularly adducts having an average of 1 to 4 moles of alkylene oxide per mol of alkanol.

The sulfur-containing acid component of the catalyst combination is sulfuric acid. As described in U.S. Pat. No. 4,721,816, the sulfuric acid is combined with one or more aluminum alcoholate or phenolate compounds. Preferably the aluminum catalyst component comprises one or more alkoxide or phenoxide compounds of the formula

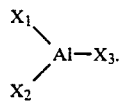

At least one of $X_1$, $X_2$, and $X_3$ represents an —OR moiety, wherein the R substituent is selected from the group consisting of alkyl and (optionally alkyl-substituted) phenyl moieties, preferably those wherein the alkyl group is in the $C_1$ to $C_{30}$ range. Particular preference exists for the use of an alkoxide in which each of the $X_1$, $X_2$ and $X_3$ substituents is an —OR group in the carbon number range from 1 to about 20, while an —OR group carbon number which corresponds to the carbon number (or carbon number range) of the alkanol reactant is generally most preferred.

The total amount of catalyst (i.e., the sum of the quantities of the sulfuric acid and aluminum components) effective for catalysis of the alkoxylation reaction in the process of the invention has not been found to be narrowly critical. For the typical practical operation, a quantity of catalyst is desirably at least about 0.01% w (percent by weight), calculated on the basis of the combined total weight of the two catalyst components relative to the weight of alkanol reactant. Preference exists for use of the catalyst in the amount of at least about 0.05% w, while an amount between about 0.1 and 1% w is considered most preferred. Substantially greater quantities of catalyst, e.g., up to about 10% w, are also very suitable.

For purposes of the process improvement of this invention it is necessary that the alkoxylation reaction mixture contain a quantity of water within a certain critical range. Furthermore, in order to realize the full benefits of the presence of such water, it is additionally necessary that the catalyst system combine the sulfuric acid and aluminum components in certain critical proportions. These two requirements for the invention can be conveniently specified in terms of restrictions upon both (a) the molar ratio of water to the aluminum catalyst component and (b) the molar ratio of sulfuric acid to the aluminum catalyst component. In such terms, it is necessary that the molar ratio of water to aluminum alcoholate and phenolate compounds present in the reaction mixture as catalyst components be in the range from about 0.1:1 to about 1.5:1, and that the molar ratio of the sulfuric acid to the aluminum alcoholate and phenolate compounds present in the reaction mixture catalyst combination be in the range from about 0.2:1 to about 0.7:1. When the proportions of water, sulfuric acid, and aluminum catalyst component fall outside these ranges, the process suffers from lower alkoxylation reaction rate and/or lower selectivity to alkoxylate. Preference has been observed for a ratio of the water to the aluminum catalyst component which is in the range from about 0.2:1 to about 0.8:1, with a ratio of sulfuric acid to aluminum catalyst component which is in the range from about 0.2:1 to about 0.6:1. Most preferred are a ratio of water to aluminum catalyst component in the range from about 0.3:1 to about 0.5:1, with a ratio of sulfuric acid to aluminum catalyst component in the range from about 0.3:1 to about 0.5:1.

The invention is further described with reference to the following examples and comparative experiments, which are intended to illustrate certain specific aspects of the invention but not to limit its broader scope.

EXAMPLES 1 AND 2 AND COMPARATIVE EXPERIMENTS A-H

Each of the examples and comparative experiments described herein was conducted according to the following general procedure. All alkoxylation reactions were carried out in a one-liter autoclave reactor. In each case, the alklyene oxide reactant consisted of ethylene oxide and the alkanol reactant was a NEODOL 23 Alcohol (trademark of and sold by Shell Chemical Company) characterized as a mixture of primary, 80% linear (20% branched carbon chain) alkanols having twelve and thirteen carbon atoms (about 40% by mol $C_{12}$ and 60% by mol $C_{13}$). Initially, the liquid alkanol reactant (150 grams, 0.774 mol) was dried for one hour at 130° C. under a nitrogen sparge to a water content of less than 100 ppm. The alkanol reactant was cooled to 100° C. and a predetermined amount of aluminum isopropoxide, "Al(O—iPr)$_3$", was added in one portion. The resulting solution was cooled to 30° C. Concentrated acid (98% w sulfuric acid ($H_2SO_4$) and 2% w water) was added. In each case, this acid was added in an amount to provide a total of 0.0050 mols of sulfuric acid. In all examples, and in some comparative experiments, additional water was added as necessary to bring the water to aluminum isopropoxide molar ratio to a predetermined level. (The mode of water introduction into the alkoxylation reaction mixture is not critical to the invention. For instance, water is suitably introduced in the form of a diluted sulfuric acid [e.g., an acid having a 93% w concentration] and/or in the form of a water addition separate from the acid addition.) The solution was then charged to the autoclave under a nitrogen atmosphere and heated to 120° C. A mixture of nitrogen and ethylene oxide was then introduced into the reactor to a total pressure of 75 psia (45 psia nitrogen and 30 psia ethylene oxide). Alkoxylation (ethoxylation) commenced immediately. Ethylene oxide was added to the reactor on demand, that is, at a rate sufficient to maintain the 75 psia pressure. The amount of ethylene oxide added over the initial 60 minutes was noted and used to calculate an average "initial rate" of reaction in terms of the average number of grams of ethylene oxide reacted per minute over this period. Temperature in the reactor was allowed to increase to 140° C. and was then maintained at that level. Ethylene oxide addition was discontinued after two mols of ethylene oxide had been charged to the reactor for each mol of alkanol reactant. The reactor was maintained at 140° C. for an additional hour to substantially consume unreacted ethylene oxide. The product mixture was then cooled, neutralized, and analyzed for alkylene oxide adduct distribution and percent weight of byproduct polyethylene glycols (PEG). In each case, the product had a very narrow range adduct distribution.

The parameters and results (initial rate and PEG formation) for each of the examples (according to the invention) and comparative experiments (not according to the invention) are presented in the following Table.

TABLE

| Example or Comparative Experiment | Mols $Al(O-iPr)_3$ | Molar Ratios | | Initial rate | PEG % w |
|---|---|---|---|---|---|
| | | $H_2$ to $Al(O-iPr)_3$ | $H_2SO_4$ to $Al(O-iPr)_3$ | | |
| 1 | 0.0167 | 1.53 | 0.30 | 3.0 | 2.2 |
| 2 | 0.0104 | 0.55 | 0.48 | 3.0 | 1.2 |
| A | 0.0104 | 2.55 | 0.48 | 1.5 | 4.0 |
| B | 0.0090 | 1.56 | 0.56 | 1.5 | 2.8 |
| C | 0.0055 | 0.09 | 0.90 | 1.6 | 2.1 |
| D | 0.0055 | 0.60 | 0.90 | 1.6 | 4.0 |
| E | 0.0055 | 1.6 | 0.90 | 1.2 | 5.9 |
| F | 0.0055 | 1.6 | 0.90 | 1.0 | 5.5 |
| G | 0.0055 | 2.6 | 0.90 | 0.8 | 6.9 |
| H | 0.0055 | 3.1 | 0.90 | 0.8 | 5.4 |

The results of these examples and comparative experiments show the importance, for high reaction rate and low formation of by-product PEG, of maintaining a ratio of water to aluminum catalyst component and a ratio of sulfuric acid to aluminum catalyst component which are within the specified limited ranges. For instance, comparison of the results of example 2 with those of comparative experiment C shows the importance of the presence of water in specified proportions; comparison of the results of examples 1 and 2 with those of experiment A shows the importance of limiting the amount of water present; and comparison of the results of examples 1 and 2 with those of experiments C–H shows the importance of limiting the proportions of sulfuric acid.

EXAMPLES 3–7

The procedures of examples 1 and 2 were again followed, utilizing different quantities of water, sulfuric acid and aluminum isopropoxide. The parameters and results for each of examples 3–7 are presented in the following Table.

TABLE

| Example | Mols $Al(O-iPr)_3$ | Molar Ratios | | Initial Rate | PEG % w |
|---|---|---|---|---|---|
| | | $H_2O$ to $Al(O-iPr)_3$ | $H_2SO_4$ to $Al(O-iPr)_3$ | | |
| 3 | 0.0106 | 0.23 | 0.47 | 4.7 | 0.5 |
| 4 | 0.0106 | 0.43 | 0.47 | 3.8 | 0.5 |
| 5 | 0.0106 | 0.43 | 0.47 | 3.5 | 0.6 |
| 6 | 0.0185 | 0.23 | 0.27 | 2.9 | 0.5 |
| 7 | 0.0185 | 0.43 | 0.27 | 2.5 | 0.4 |

The results of examples 3 to 7 illustrate both the very high rate and the low PEG formation which are realized by operation of the invention under preferred ratios of water to aluminum catalyst component and of sulfuric acid to aluminum catalyst component.

I claim as my invention:

1. In the process for the preparation of narrow-range alkanol alkoxylates by contacting and reacting an alkylene oxide reactant comprising one or more $C_2$ to $C_4$ vicinal alkylene oxides with an alkanol reactant comprising one or more $C_6$ to $C_{30}$ alkanols in the presence of a catalytically effective amount of a catalyst prepared by contacting (i) sulfuric acid and (ii) an aluminum catalyst component comprising one or more compounds selected from the group consisting of aluminum alcoholates and aluminum phenolates, the improvement which comprises carrying out the said contact and reaction in the presence of a catalyst prepared by contacting the sulfuric acid and the aluminum catalyst component in a molar ratio of sulfuric acid to aluminum alcoholate and phenolate compounds which is in the range from about 0.2:1 to about 0.7:1 and further in the presence of a quantity of water in a molar ratio of water to aluminum alcoholate and phenolate compounds which is in the range from about 0.1:1 to about 1.5:1.

2. The process of claim 1, wherein the molar ratio of sulfuric acid to aluminum alcoholate and phenolate compounds is in the range from about 0.2:1 to about 0.6:1 and the molar ratio of water to aluminum alcoholate and phenolate compounds is in the range from about 0.2:1 to about 0.8:1.

3. The process of claim 2, wherein the molar ratio of sulfuric acid to aluminum alcoholate and phenolate compounds is in the range from about 0.3:1 to about 0.5:1 and the molar ratio of water to aluminum alcoholate and phenolate compounds is in the range from about 0.3:1 to about 0.5:1.

4. In the process for the preparation of narrow-range alkanol ethoxylates by contacting and reacting an alkylene oxide reactant consisting essentially of ethylene oxide with an alkanol reactant comprising one or more $C_6$ to $C_{30}$ primary mono-hydric alkanols in the presence of a catalytically effective amount of a catalyst prepared by contacting (i) sulfuric acid and (ii) an aluminum catalyst component comprising one or more compounds selected from the group consisting of aluminum alcoholates and aluminum phenolates, the improvement which comprises carrying out the said contact and reaction in the presence of a catalyst prepared by contacting the sulfuric acid and the aluminum catalyst component in a molar ratio of sulfuric acid to aluminum alcoholate and phenolate compounds which is in the range from about 0.2:1 to about 0.7:1 and further in the presence of a quantity of water in a molar ratio of water to aluminum alcoholate and phenolate compounds which is in the range from about 0.1:1 to about 1.5:1.

5. The process of claim 4, wherein the molar ratio of sulfuric acid to aluminum alcoholate and phenolate compounds is in the range from about 0.2:1 to about 0.6:1 and the molar ratio of water to aluminum alcoholate and phenolate compounds is in the range from about 0.2:1 to about 0.8:1.

6. The process of claim 5, wherein the molar ratio of sulfuric acid to aluminum alcoholate and phenolate compounds is in the range from about 0.3:1 to about 0.5:1 and the molar ratio of water to aluminum alcoholate and phenolate compounds is in the range from about 0.3:1 to about 0.5:1.

7. The process of claim 4, wherein the alkanol reactant comprises one or more $C_8$ to $C_{20}$ primary monohydric alkanols.

8. The process of claim 7, wherein the molar ratio of sulfuric acid to aluminum alcoholate and phenolate compounds is in the range from about 0.2:1 to about 0.6:1 and the molar ratio of water to aluminum alcoholate and phenolate compounds is in the range from about 0.2:1 to about 0.8:1.

9. The process of claim 7, wherein the alkanol reactant comprises one or more $C_{11}$ to $C_{16}$ primary monohydric alkanols.

10. The process of claim 9, wherein the molar ratio of sulfuric acid to aluminum alcoholate and phenolate compounds is in the range from about 0.3:1 to about 0.5:1 and the molar ratio of water to aluminum alcoholate and phenolate compounds is in the range from about 0.3:1 to about 0.5:1.

11. The process of claim 1, wherein the aluminum catalyst component comprises one or more compounds having the formula

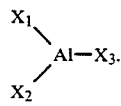

wherein at least one of $X_1$, $X_2$ and $X_3$ represents an —OR moiety, wherein R is selected from the group consisting of $C_1$ to $C_{30}$ alkyl, phenyl and alkyl-substituted phenyl moieties.

12. The process of claim 11, wherein at least one of $X_1$, $X_2$, and $X_3$ represents an —OR moiety wherein R is $C_1$ to $C_{30}$ alkyl.

13. The process of claim 12, wherein each of $X_1$, $X_2$, and $X_3$ represents an —OR moiety wherein R is an alkyl group having a carbon number in the range from 1 to 30.

14. The process of claim 5, wherein the aluminum catalyst component comprises one or more compounds having the formula

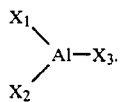

wherein at least one of $X_1$, $X_2$ and $X_3$ represents an —OR moiety, wherein R is selected from the group consisting of $C_1$ to $C_{30}$ alkyl, phenyl and alkyl-substituted phenyl moieties.

15. The process of claim 14, wherein at least one of $X_1$, $X_2$, and $X_3$ represents an —OR moiety wherein R is $C_1$ to $C_{30}$ alkyl.

16. The process of claim 15, wherein each of $X_1$, $X_2$, and $X_3$ represents an —OR moiety wherein R is an alkyl group having a carbon number in the range from 1 to 30.

17. In the process for the preparation of narrow-range alkanol ethoxylates by contacting and reacting an alkylene oxide reactant consisting essentially of ethylene oxide with an alkanol reactant comprising one or more $C_8$ to $C_{20}$ predominantly linear, primary mono-hydric alkanols in the presence of a catalytically effective amount of a catalyst prepared by contacting (i) sulfuric acid and (ii) an aluminum catalyst component comprising one or more compounds having the formula

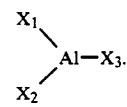

wherein at least one of $X_1$, $X_2$ and $X_3$ represents an —OR moiety, wherein R is selected from the group consisting of $C_1$ to $C_{30}$ alkyl, phenyl and alkyl-substituted phenyl moieties, the improvement which comprises carrying out the said contact and reaction in the presence of a catalyst prepared by contacting the sulfuric acid and the aluminum catalyst component in a molar ratio of sulfuric acid to aluminum alcoholate and phenolate compounds which is in the range from about 0.2:1 to about 0.6:1 and further in the presence of a quantity of water in a molar ratio of water to aluminum alcoholate and phenolate compounds which is in the range from about 0.2:1 to about 0.8:1.

18. The process of claim 17, wherein each of $X_1$, $X_2$, and $X_3$ represents an —OR moiety wherein R is an alkyl group having a carbon number in the range from 1 to 30.

19. The process of claim 18, wherein the molar ratio of sulfuric acid to aluminum alcoholate and phenolate compounds is in the range from about 0.3:1 to about 0.5:1 and the molar ratio of water to aluminum alcoholate and phenolate compounds is in the range from about 0.3:1 to about 0.5:1.

20. The process of claim 1, wherein the alkylene oxides are contacted and reacted with the alkanols in a molar ratio of up to about 4 mols of alkylene oxides per mol of alkanols.

21. The process of claim 4, wherein the ethylene oxide is contacted and reacted with the alkanols in a molar ratio of up to about 4 mols of ethylene oxide per mol of alkanols.

22. The process of claim 8, wherein the ethylene oxide is contacted and reacted with the alkanols in a molar ratio of up to about 4 mols of ethylene oxide per mol of alkanols.

23. The process of claim 17, wherein the ethylene oxide is contacted and reacted with the alkanols in a molar ratio of up to about 4 mols of ethylene oxide per mol of alkanols.

24. The process of claim 19, wherein the ethylene oxide is contacted and reacted with the alkanols in a molar ratio of up to about 4 mols of ethylene oxide per mol of alkanols.

* * * * *